US00PP09457P

United States Patent [19]

Olesen et al.

[11] Patent Number: Plant 9,457

[45] Date of Patent: Feb. 27, 1996

[54] SHRUB ROSE PLANT NAMED 'POULSHINE'

[75] Inventors: Pernille Olesen; Mogens N. Olesen, both of Fredensborg, Denmark

[73] Assignee: De Vor Nurseries, Inc., Watsonville, Calif.

[21] Appl. No.: 380,123

[22] Filed: Jan. 30, 1995

[51] Int. Cl.[6] ..... A01H 5/00

[52] U.S. Cl. ..... Plt./1

[58] Field of Search ..... Plt./1, 7.1, 9, 26

*Primary Examiner*—Howard J. Locker

*Attorney, Agent, or Firm*—Christie, Parker & Hale

[57] ABSTRACT

A new low growing shrub rose producing light pink flowers.

1 Drawing Sheet

SUMMARY OF THE INVENTION

The present invention relates to a new and distinct variety of shrub rose which was originated by our crossing as seed and pollen parents two unnamed and undistributed seedlings of our creation. The varietal denomination of this new rose is 'Poulshine'.

Among the novel characteristics possessed by this new variety which distinguish it from its parents and all other varieties of which we are aware are its low growing growth habit producing small soft pink flowers.

Asexual reproduction by budding of the new variety as performed in Watsonville, Calif., shows that the foregoing and other distinguishing characteristics come true to form and are established and transmitted through succeeding propagations. Other useful forms of asexual reproduction may be also employed.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—Unnamed, unpatented seedling.

Class: Low growing shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Pointed.

(3) *Color.*—When sepals first divide, bud color is near 47D.

(4) *Sepals: Longer than and about* 1 to 1.5 cm; reflexing when bloom opens. Color: Near 146B.

(5) *Peduncle.*—Length: About 2 to about 2.5 cm. Aspect: Very small hairs and some very small prickles. Strength: Erect, sturdy. Color: Near 146C.

(6) Bracts.—3 to 7 per cluster; near 137A; leaf-like; located about 1.5 to 2 cm below calyx.

B. Bloom:

(1) *Size.*—Average size when fully expanded — about 3 cm to about 3.5 cm.

(2) *Borne.*—Sprays of about 3 to 11 blooms.

(3) *Form.*—Informal.

(4) *Petalage.*—Number of petals under normal conditions — about 10 to 12.

(5) *Color* (⅓ to ½ open).—Outer petals — Top surface: near 38D; Undersurface: near 48D. Inner petals — Top surface: near 37D; Undersurface: near 54D. Base of petals — (point of attachment): Near 7A. General tonality from a distance: Pink.

(6) *Color (fully open).*— Outer petals — Top surface: near 51D; Undersurface: near 54C. Inner petals — Top surface: near 50D; Undersurface: near 55B. Base of petals: (point of attachment): Near 8A. General tonality from a distance: Pink.

(7) Color change.—As bloom ages: Lightens from bud color when sepals first divide, then darkens at about ½ to ⅓ open. Petal top surface: Darkens from near 38D to near 51D. Petal undersurafce: Darkens from near 48D to near 54C. General tonality at a distance: Pink.

C. Petals:

(1) *Texture.*—Thick.

(2) Appearance.—Inside semi-velvety and outside matte.

(3) *Form.*—Wedge-shaped with pointed apex.

(4) *Arrangement.*—Informal.

(5) *Petaloids.*—Few.

(6) *Fragrance.*—Very slight fruity fragrance.

(7) *Lasting quality.*—Not suitable for cut flowers.

(8) *Persistence.*—Petals drop off cleanly.

REPRODUCTIVE ORGANS

A. Stamens:

(1) *Arrangements.*—Introrse around styles, near 13A.

(2) *Anthers.*—Color near 17B.

(3) *Filaments.*—Color near 16B.

(4) *Pollen.*—Color — near 17B.

B. Pistils:

(1) *Styles.*—Bunched, evenly together, short.

(2) *Stigmas.*—Color tip near 11A; center near 35B; base near 154D.

C. Characteristics of hips: Not observed.

PLANT

A. Form: Low, compact, spreads outwardly.

B. Growth: Vigorous; height attained about 22 cm to about 33 cm at first season.

C. Foliage: Few compound 3, some compound 5 and mostly compound 7 leaflets.

(1) *Size.*—Small.

(2) *quantity.*—Abundant.

(3) *Color.*—New foliage — upper side near 137A; underside near 147B; mature foliage — upper side near 139A, underside near 147B.

(4) *Shape.*—Narrow, curled longitudinally.

(5) *Texture.*—Upper side slightly matte; underside smooth.

(6) *Edge.*—Serrate.

(7) Serration.—Denticulate.

(8) Color — medium green.

(9) Stipules.—Adnate with glandular edging.

(10) *Rachis.*—Very small prickles on underside.

(11) *Petioles.*—Top near 199A, underside near 146D.

(12) *Auricle: Pointed and tipped with glands, thin.*

(13) *Resistance to disease*: Very resistant to blackspot, mildew and rust.

D. Wood:

(1) *New wood.*—Color near 166B, bark smooth.

(2) *Old wood.*—Color near 146A to 146B, bark smooth.

E. Flower Stem: About 15 cm to about 23cm from last cut.

F. Thorns:

(1) *Thorns.*—Quantity: On main stalk average, few on laterals from basal canes. Form: Thin, slightly curved downward. Length: Medium. Color: When young near 160A in center with near 176B on tips and base. Position: Irregular.

(2) *Prickles.*—None.

G. Winter hardiness: Winter hardy in Watsonville, Calif.

We claim:

1. A new and distinct low growing shrub rose variety, substantially as shown and described.

* * * * *

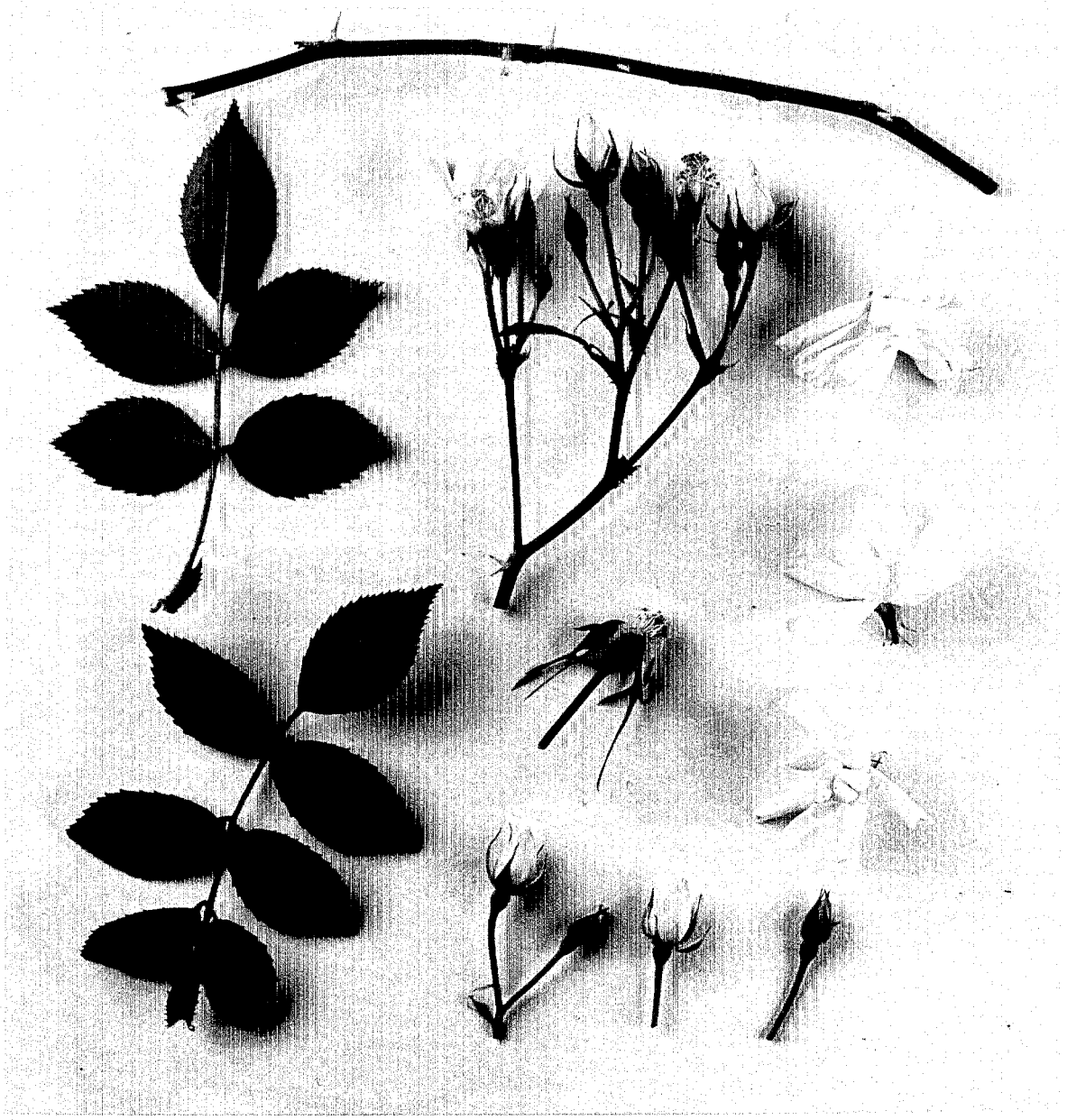

UNITED STATES PATENT AND TRADEMARK OFFICE

CERTIFICATE OF CORRECTION

PATENT NO. : Plant 9,457

DATED : February 27, 1996

INVENTOR(S) : Pernille Olesen; Mogens N. Olesen

It is certified that error appears in the above-indentified patent and that said Letters Patent is hereby corrected as shown below:

Column 3, line 8, change "*quantity.*" to -- *Quantity.* --.

Column 3, line 18, before "Color" insert
-- *Leaf Stem.*— --.

Signed and Sealed this

Twenty-second Day of October, 1996

*Attest:*

*Attesting Officer*

Bruce Lehman

BRUCE LEHMAN

*Commissioner of Patents and Trademarks*